US008133920B2

(12) United States Patent  
Johnson et al.

(10) Patent No.: US 8,133,920 B2
(45) Date of Patent: *Mar. 13, 2012

(54) GROWTH HORMONE-CONTAINING FORMULATION AND METHOD OF USE

(75) Inventors: Louis B Johnson, Troy, AL (US); Jeffery L Peel, Malvern, AL (US)

(73) Assignee: Accelegrow Technologies, Inc., West Point, GA (US)

( * ) Notice: Subject to any disclaimer, the term of this patent is extended or adjusted under 35 U.S.C. 154(b) by 353 days.

This patent is subject to a terminal disclaimer.

(21) Appl. No.: 12/292,757

(22) Filed: Nov. 25, 2008

(65) Prior Publication Data

US 2009/0082207 A1    Mar. 26, 2009

Related U.S. Application Data

(63) Continuation of application No. 11/701,510, filed on Feb. 2, 2007, now abandoned, which is a continuation-in-part of application No. 11/211,424, filed on Aug. 26, 2005, now abandoned.

(51) Int. Cl.
| | |
|---|---|
| *A01N 33/18* | (2006.01) |
| *A01N 33/24* | (2006.01) |
| *A61K 31/04* | (2006.01) |
| *A61K 9/00* | (2006.01) |

(52) U.S. Cl. ................ 514/740; 514/970; 424/400

(58) Field of Classification Search .................. 514/740, 514/970; 424/400

See application file for complete search history.

(56) References Cited

U.S. PATENT DOCUMENTS

| 4,169,717 | A | 10/1979 | Ashmead | |
|---|---|---|---|---|
| 4,816,568 | A * | 3/1989 | Hamilton et al. | ............ 530/399 |
| 6,251,878 | B1 | 6/2001 | Strickland et al. | |
| 6,458,546 | B1 | 10/2002 | Baker | |
| 2002/0053229 | A1 | 5/2002 | Varshovi | |
| 2005/0123499 | A1* | 6/2005 | Majmudar | ..................... 424/74 |
| 2005/0234041 | A1 | 10/2005 | Tomazic et al. | |
| 2005/0288188 | A1 | 12/2005 | Volgas et al. | |
| 2007/0020342 | A1 | 1/2007 | Modak et al. | |

FOREIGN PATENT DOCUMENTS

WO        02/082902        10/2002

OTHER PUBLICATIONS

SeaCrop Liquid kelp Extract (published on Feb. 19, 1999 at http://web.archive.org/web/19990219170SI/http://www.noamkelp.com/scprod.html.

* cited by examiner

*Primary Examiner* — Johann Richter
*Assistant Examiner* — Mei-Ping Chui
(74) *Attorney, Agent, or Firm* — Clark & Brody

(57) ABSTRACT

A growth hormone formulation includes an enzyme inactivating component and a preservative. The formulation can also include a fertilizing additive, and a surfactant. The growth hormone can be a natural one such as that found in kelp or a synthetic one or a combination of both.

21 Claims, No Drawings

GROWTH HORMONE-CONTAINING FORMULATION AND METHOD OF USE

This application is a continuation of application Ser. No. 11/701,510 filed Feb. 2, 2007 now abandoned, which is a continuation in part of application Ser. No. 11/211,424 filed Aug. 26, 2005 now abandoned, both being incorporated herein by reference, which claims the benefit of provisional application No. 60/610,202 filed on Sep. 16, 2004.

TECHNICAL FIELD,

The present invention relates to a liquid kelp formulation and a method of making, and in particular to a formulation that includes an enzyme inactivating component and preservative.

BACKGROUND ART

Kelp, commonly referred to as seaweed, grows along coastlines around the world and is botanically classified as algae. The use of liquid kelp as a growth stimulant is well known in the agricultural industry. This seaplant is rich in micronutrients and natural growth hormones, including cytokinins, auxins and gibberellins, which stimulate cell division and larger root systems. Kelp extracts can be applied as a foliar spray on plants and the like, or on soil for later contact and absorption by root structures. An extract applied to land plants is known to accelerate growth, increase fruiting and flowering, intensify color, and provide resistance to disease, insects, drought, and frost. Many commercial liquid formulations of kelp are available for use in the agricultural industry and can be found in various retail and wholesale outlets, as well as through the internet. These kelp formulations are basically an extract of kelp diluted with water, and may contain other components as the manufacturer of the formula may see fit. Examples of formulations include those sold at the Gardens Alive website www.gardensalive.com, Sea Crop Liquid Kelp Extract (to be diluted in water), and the like.

It is also known to use kelp in tablet or capsule form to treat different health problems. One problem with present day liquid kelp materials is the short shelf life of the formulation. When the kelp is combined with water and other components, bacteria or other impurities present in the water or other additives break down the growth hormones found in the kelp, thus rendering them ineffective over time.

Thus, a need exists to provide improved kelp formulations, including those that have extended shelf lives. The present invention responds to this need by providing a liquid kelp formulation that has an increased shelf life.

SUMMARY OF THE INVENTION

One object of the present invention is an improved liquid kelp formulation.

Another object of the invention is a method of making the liquid formulation.

Yet another object is a system of providing kelp for agricultural purposes, but without subjecting the kelp to prolonged exposure to water and/or other additives.

Other objects and advantages will become apparent as a description thereof proceeds.

In satisfaction of the foregoing objects and advantages, the invention is an improvement in liquid kelp formulations by the presence of an effective amount of an enzyme inactivating component selected from the group consisting of sarcosine, manganese chloride, sodium dodecyl sulfate, sodium lauryl sarcosinate, grape seed oil, pine bark extract, grape leaf, black currant, passion flower, and *chlorella vulgaris* to reduce the degradation of growth hormones in the liquid kelp formulation. A preservative is also included, the preservative amount effective to retard growth of bacteria, fungi, and/or mold in the liquid kelp formulation. The enzyme inactivating component preferably ranges from zero and up to 5.00% by weight of the formulation, more preferably between 0.25% and 3.0%, and most preferably between 0.5 to 1.5%. A preferred enzyme inactivating component is sarcosine.

The preservative is preferably a food grade preservative and/or the preservative is in a range of from 0.10 to 1% by weight, more preferably between 0.15% and 0.50%, and most preferably around 0.2-0.3%. The preservative is preferably one of methyl paraben, propyl paraben, and diazolidinyl urea.

The formulation can also include an effective amount of a surfactant for wetting purposes, preferably a nonionic surfactant such as an alcohol ethoxylate. The alcohol ethoxylate preferably has 9 or more moles of ethoxylation.

The formulation can also include a source of nitrogen, phosphorous, or potassium, and if nitrogen is used, it is preferred to use a compound containing ammonia or urea.

The invention entails the method of using the formulation wherein the liquid kelp formulation is applied to plant, for example, by direct application to the plants themselves, including to the foliage and/or roots of the plants, and to the soil in the vicinity of the plants.

Another aspect of the invention entails improvements in the method of applying a liquid kelp formulation to plants. In this aspect, the kelp is provided into a solid form, made into a solution, and immediately applied to plants or soil. This method can be modified by including the enzyme inactivating component and/or preservative discussed above. The enzyme inactivating component and/or preservative can be present as part of either the solid kelp or the water prior to the adding step. In another alternative, the enzyme inactivating component and/or preservative could be maintained as separate components and added either individually or together to either the water or a water-kelp solution.

The invention also entails the use of synthetic growth hormones in place of or with the natural hormones found in kelp. In this embodiment, the kelp can be replaced with or combined with synthetic growth hormones for treating plants, seeds, and the like. The synthetic growth hormone-containing formulation can be applied to seeds, plants, etc, in a similar manner as disclosed for the formulation containing kelp.

DESCRIPTION OF THE PREFERRED EMBODIMENTS

The present invention is an improvement over the kelp formulations found in the prior art. By practicing the invention, the breakdown of the growth hormones found in kelp is slowed or eliminated as a result of additives combined with the kelp or the manner in which the kelp is combined with water and additives.

The liquid kelp formulation or system of the invention can be applied to plants or any vegetation that would require a boost in growth or benefit from other effects attributable to kelp. The term "plants" is intended to encompass any and all vegetation in this regard that would benefit from application of kelp. Examples includes vegetables, legumes, flowers, shrubs, trees, grasses, fruits, vines, etc., and their roots in the event that the formulation is used as a root dip or applied to soil to improve root structure. The inventive formulation could also be employed to treat seeds, e.g., coating or treating the seeds with the formulation by spraying, immersing, or the like.

In one embodiment of the invention, an additive-containing kelp formulation is made that has extended shelf life, and can then be used at a later time to stimulate growth in plants and the like.

In another embodiment, a system is provided that produces an aqueous liquid formulation, with or without various additives. As part of this system, the kelp is maintained separately from liquid formulation until the formulation as made is to be applied in a given manner. The kelp, in virtually any solid form, can be added to the aqueous liquid formulation. The formulation can contain additives when combined with the kelp, can be additive free, or can have the additives added after kelp addition. For example, the solid form of the kelp could be a capsule, a pellet, granule, tablet, meal, or other solid form. The additives can be those employed with the liquid formulation of the invention, or other known additives that are commonly found in kelp formulations.

Turning to the liquid kelp formulation aspect of the invention, one additive is an enzyme inactivating component such as sarcosine, manganese chloride, sodium dodecyl sulfate, sodium lauryl sarcosinate, grape seed oil, pine bark extract, grape leaf, black currant, passion flower, and *chlorella vulgaris* with sarcosine being a preferred enzyme inactivating component. An effective amount is employed in the liquid kelp formulation such that the growth hormones therein do not break down as fast over time as they would without the inactivating additive. A more preferred amount is up to 5.0% by weight of the total formulation, with more preferred ranges between 0.25 and 3.0%, and most preferably between 0.5 to 1.5%. Enzyme inactivating compounds are disclosed in U.S. Pat. No. 6,458,546 to Baker et al. (Baker), which is herein incorporated in its entirety by reference. It should be noted that the Baker patent references SARKOSYL as one of the enzyme inactivating ingredients. SARKOSYL is actually a trademark, and the proper chemical reference is sarcosine, as noted in Hawley's The Condensed Chemical Dictionary, Eighth Edition, pp. 774 and 775. The chemical name for sarcosine is methyl glycocoll aminoacetic acid. The Baker patent is not relevant to the present invention and is concerned with the preservation of DNA in samples, and discloses the addition of the enzyme inactivating components in combination with a divalent metal chelator such as EDTA, EGTA, and BAPTA, and at least one chelator enhancing component such as lithium chloride, guanidine, sodium salicylate, sodium perchlorate, and sodium thiocyanate, each in specified amounts. It is contemplated that the chelator and chelator-enhancing component of Baker could be employed with the effective amount of the enzyme inactivating components that is utilized in the present invention if so desired, and in the amounts taught by Baker.

Another additive for the liquid kelp formulation is a preservative in an amount effective to preserve the formulation and resist bacterial, fungi, and/or mold growth. Preferred ranges include from 0.10 to 1% by weight, more preferred ranges include 0.15% to 0.5% with a target of around 0.2-0.3%. Virtually any known preservative can be employed in the formulation, with examples including those using propyl paraben, methyl paraben, and diazolidinyl urea, e.g., Germaben II. Another specific preservative that can be used is Dantoguard® manufactured by Lonza, see www.Lonza.com. Dantoguard® Plus is another preservative adaptable for use in the invention, this particular preservative more adapted for battling fungi and bacteria.

Since the kelp could be sprayed on food bearing plants, it is important to ensure that the additives are food safe. In this regard, if the liquid kelp is intended to be sprayed on plants or other vegetation or come into contact with any vegetation that may be eaten or bear fruit, the preservative should be a food grade preservative such as the methyl or propyl parabens mentioned above.

If so desired, the kelp formulation could be enhanced with additional fertilizing additives or agents that provide nitrogen, phosphorous, or potassium, or other micronutrients such as those containing trace elements like boron, selenium, zinc, and the like. One example would be an amount of ammonia to provide additional nitrogen. The amount should be sufficient to have an effect on the treated plants, with a preferred amount being up to about 10.0% by weight of the formulation, and more preferably 5-10% by weight. One example would be a formulation of 3-3-3 of nitrogen, phosphorous and potassium.

One example of a preferred formulation is as follows:

| Component | Percentage by weight | 55 gallons (in lbs. except for water) | 5 gallons (in lbs.) |
|---|---|---|---|
| Powdered kelp | 5.0 | 23 | 2.0 |
| Nipasol-m-sodium[1] | 0.3 | 1.4 | 0.1 |
| Ammonia[2] | 0.5% | 2.3 | 0.2 |
| Sarcosine | 1.0 | 4.6 | 0.4 |
| Water | 93.2 | 51 gallons | 37.2 |

[1]Nipasol-m-sodium is a propyl paraben preservative.
[2]Ammonia is added as an additional fertilizer boost.

Another preservative that could be used as part of the formulation is Nipacide Bit-20 made by Clariant Corporation of Charlotte, N.C. While ammonia is exemplified here, other fertilizers such as urea could be used.

In formulating the liquid kelp, it is preferred to dissolve the preservative into the water first while taking the necessary precautions to avoid inhaling any of the preservative, and then add the remaining components, although the components could be added in any order if so desired.

The liquid kelp formulation can be made in a concentrated form which would be diluted by the end user, or in a ready to use concentration as exemplified by the table above, with either of these modes of delivery well known in the art. When making a concentrate, the weight percentages of the various additives would be adjusted so that when the concentrate is diluted, the percentages still fall within the ranges given above for the broad and more preferred embodiments of the invention.

The manner of application of the liquid kelp formulation can be any type known in the art. For example, the formulation can be used as a foliar spray, or for dipping plant roots, or applied directly to soil so that the formulation can interact with roots of the plants in the soil, or for treating seeds such as by coating, immersion, or the like.

It should also be understood that the formulation can include one or more surfactants for wetting if so desired. When using a surfactant, virtually any surfactant that imparts wetting to the formulation can be used. A preferred class of surfactants includes nonionic types such as alcohol ethoxylates, with preferred moles of ethoxylation being about 9 or more.

The kelp can be obtained from any commercial source of kelp for use in the invention, either in making the liquid kelp formulation or a solid form for later dissolution and use.

As mentioned above, another aspect of the invention is a system entailing making of a liquid kelp formulation by providing a solid form of kelp and dissolving it in water. The water can contain other additives as desired. Alternatively, the kelp in solid form could contain the additives, as desired. The additives can be those known in the art such as fertilizing additives, or the additives noted above.

In an alternate mode of this aspect of the invention, the additives could be separate from the water and solid kelp and added to the water, either before or after dissolving the kelp.

This system of the invention is advantageous in that the kelp is kept separate from the water and its impurities until it is desired to apply the kelp to a given plant or area. Thus, a potent kelp liquid is provided that does not suffer from potency loss like liquid kelps that have been stored over time do. The form of the solid kelp can be any type, e.g., tablet, pill, capsule, powder, granule, pellet, cake, or the like. The form of the additives can also be any type, liquid or solid. As noted above, the additives can be any type typically found in known kelp formulations or they can include those mentioned above in terms of the enzyme inactivating component, preservative, and/or surfactant and fertilizer. It is anticipated that the enzyme inactivating component may be optional in this mode of the invention since the kelp would be used immediately after forming the liquid, and the breakdown of growth hormones would not be the significant problem that it is with prior art kelp liquids. The preservative may also be optional, but could be added to the solid kelp to preserve its shelf life.

Another embodiment of the invention entails the use of the enzyme inactivating component in combination with a formulation containing a synthetic growth hormone instead of the above-mentioned liquid or solid kelp formulation that contain natural growth hormones such as cytokinins, auxins, and gibberellins. One example of these synthetic growth hormones is Technical Kinetin, which is sold as 98.5 wt. % cytokinin and 1.5 wt. % other ingredients, and is available from Stoller USA of Houston Tex. Other materials from Stoller USA that are synthetic growth hormones include Technical Gibberellic Acid ($GA_3$), which contains 92 wt. % of gibberellic acid and 8 wt. % other ingredients material, and Indole-3-butyric Acid, which contains 99 wt. % indole-3-butyric acid (auxin) and 1 wt. % other ingredients. Other synthetic growth hormones include abscisic acid (ABA), jasmonic acid, ethylene, 1-naphthylacetic acid (NM) brassinosteriods, salicylic acid (SA), oligogalacturonides (pectin-derived polymers), xyloglucan (hemicellulose-derived polymers), and benzyladenine (BA). It should be understood that the Stoller USA products and those recited above are only examples of the types of synthetic hormones that can be employed and others that are commercially available are also within the scope of the invention.

The synthetic growth hormone can be used with the enzyme inactivating component and preservative in any number of ways. The synthetic growth hormone is normally provided in liquid form can be combined with the enzyme inactivating component and preservative and sprayed or otherwise applied to the intended material for treatment. If the synthetic growth hormone is in solid form such as a powder, it can be combined with the enzyme inactivating component and preservative formulation and then made into a solution or added to a solution containing the enzyme inactivating component and preservative. In addition, the synthetic growth hormones can also be employed in the same manner as described above for the kelp in both solid and liquid forms.

Using synthetic growth hormones in substitution of kelp offers the advantages that the possible contaminants in kelp are avoided, and supply problems which may occur since kelp must be harvested can be eliminated. Since kelp has filtering properties when it is in water, it can take up unwanted materials such as heavy metals due to ocean pollution. While there are ample sources of kelp and the contamination of kelp is not believed to be a severe problem, using synthetic hormones eliminates any risk of the presence of unwanted materials in the kelp. Also, since the supply of kelp could be disrupted to do economic or natural events, its availability can fluctuate. The manufacture of synthetic growth hormones is not subject to such influences, and it can always be readily available if needed.

As yet another embodiment, the synthetic growth hormones could be combined with the kelp when using the enzyme inactivating component and preservative if so desired. The weight ratio of the two could vary from just a minor amount of synthetic growth hormone, e.g., less than 1 percent, to a predominance of the synthetic growth hormone, e.g., greater than 99%.

As such an invention has been disclosed in terms of preferred embodiments thereof, which fulfills each and every one of the objects of the invention as set forth above, and provides a growth hormone-containing formulation and method of use.

Of course, various changes, modifications and alterations from the teachings of the present invention may be contemplated by those skilled in the art without departing from the intended spirit and scope thereof. It is intended that the present invention only be limited by the terms of the appended claims.

We claim:

1. In a growth hormone-containing formulation, wherein the growth hormone is the main active ingredient of the growth hormone-containing formulation and is a growth stimulant for plants, the improvement comprising an effective amount of sarcosine as an enzyme inactivating component to reduce the degradation of growth hormones in the growth hormone-containing formulation, and a preservative in an amount effective to retard growth of bacteria, fungi, and/or mold in the growth hormone-containing formulation.

2. The formulation of claim 1, wherein the enzyme inactivating component ranges up to 5.0% by weight of the formulation.

3. The formulation of claim 2, wherein the enzyme inactivating component ranges between 0.25 and 3.0% by weight of the formulation.

4. The formulation of claim 1, wherein the preservative is a food grade preservative.

5. The formulation of claim 4, wherein the preservative is in the range of from 0.10 to 1.0% by weight of the formulation.

6. The formulation of claim 5, wherein the preservative is in the range of from 0.15 to 0.5% by weight of the formulation.

7. The formulation of claim 1, wherein the preservative is one of methyl paraben, propyl paraben and diazolidinyl urea.

8. The formulation of claim 1, further comprising an effective amount of a surfactant for wetting purposes.

9. The formulation of claim 8, wherein the surfactant is an alcohol ethoxylate.

10. The formulation of claim 9, wherein the alcohol ethoxylate has 9 or more moles of ethoxylation.

11. The formulation of claim 1, further comprising a plant fertilizing agent comprising nitrogen, phosphorous, or potassium.

12. The formulation of claim 11, comprising ammonia as the nitrogen source.

13. A method for plant growth stimulation comprising applying a growth hormone-containing formulation to plants or seeds, wherein the growth hormone-containing formulation comprises an amount of growth hormone that is a growth stimulant for plants, an effective amount of sarcosine as an enzyme inactivating component to reduce the degradation of growth hormones in the growth hormone-containing formulation, and a preservative in an amount effective to retard growth of bacteria, fungi, or mold in the growth hormone-containing formulation.

14. The method of claim 13, wherein the formulation is applied directly to the plants or seeds, or applied to the plants or seeds indirectly via application to soil.

15. The formulation of claim 1, wherein the growth hormone-containing formulation contains a synthetic growth hormone.

16. The method of claim 13, wherein the growth hormone-containing formulation contains a synthetic growth hormone.

17. The method of claim 16, wherein the growth hormone-containing formulation further contains a natural kelp.

18. The formulation of claim 3, wherein the enzyme inactivating component ranges between 0.5 and 1.5% by weight of the formulation.

19. The formulation of claim 6, wherein the preservative is in the range of from around 0.2 to 0.3% by weight of the formulation.

20. The formulation of claim 8, wherein the surfactant is a non-ionic surfactant.

21. The method of claim 13, wherein the growth hormone is the main active ingredient of the growth hormone-containing formulation.

* * * * *

UNITED STATES PATENT AND TRADEMARK OFFICE
CERTIFICATE OF CORRECTION

| | |
|---|---|
| PATENT NO. | : 8,133,920 B2 |
| APPLICATION NO. | : 12/292757 |
| DATED | : March 13, 2012 |
| INVENTOR(S) | : Louis B. Johnson and Jeffery L. Peel |

It is certified that error appears in the above-identified patent and that said Letters Patent is hereby corrected as shown below:

Title Page:

Item 62 Related U.S. Application Data should be added to include U.S. Provisional Application No. 60/610,202, filed on September 16, 2004

Signed and Sealed this
Twenty-third Day of July, 2013

Teresa Stanek Rea
*Acting Director of the United States Patent and Trademark Office*